United States Patent
Stadlwieser et al.

(10) Patent No.: US 8,845,863 B2
(45) Date of Patent: Sep. 30, 2014

(54) ALKYLENE OXIDE PURIFICATION PROCESSES AND SYSTEMS

(75) Inventors: Clarence P. Stadlwieser, Sherwood Park (CA); Bernie B. Osborne, Hurricane, WV (US); John P. Dever, Kenner, LA (US); Harvey E. Andresen, Luling, LA (US); Michael L. Hutchison, Poca, WV (US); Gary L. Culp, Kenna, WV (US); Donald R. Culp, legal representative, Baltimore, MD (US); Steven R. Osborne, Luling, LA (US); Liping L. Zhang, Hurricane, WV (US); Michael Habenschuss, South Charleston, WV (US); Andrew Addie, Louisville, KY (US)

(73) Assignee: Dow Technology Investments LLC, Midland, MI (US)

( * ) Notice: Subject to any disclaimer, the term of this patent is extended or adjusted under 35 U.S.C. 154(b) by 1050 days.

(21) Appl. No.: 12/460,752

(22) Filed: Jul. 24, 2009

(65) Prior Publication Data

US 2010/0036170 A1 Feb. 11, 2010

Related U.S. Application Data

(60) Provisional application No. 61/137,514, filed on Jul. 31, 2008, provisional application No. 61/137,494, filed on Jul. 31, 2008, provisional application No. 61/137,517, filed on Jul. 31, 2008, provisional application No. 61/137,493, filed on Jul. 31, 2008, provisional application No. 61/137,485, filed on Jul. 31, 2008.

(51) Int. Cl.
- *B01D 3/00* (2006.01)
- *B01D 3/14* (2006.01)
- *C07D 301/32* (2006.01)
- *C07D 303/00* (2006.01)
- *C07C 43/00* (2006.01)
- *C07C 31/18* (2006.01)

(52) U.S. Cl.
CPC .................................. *C07D 301/32* (2013.01)
USPC ............... 202/159; 203/28; 203/99; 549/512; 549/541; 568/672; 568/852

(58) Field of Classification Search
USPC .................. 549/541, 512; 203/91, 92, 28, 99; 202/159; 568/672, 852
See application file for complete search history.

(56) References Cited

U.S. PATENT DOCUMENTS 2,615,901 A 10/1952 McClellan
2,697,104 A 12/1954 Lowe et al.
(Continued)

FOREIGN PATENT DOCUMENTS

CZ 104663 8/1962
DE 1165567 3/1964
(Continued)

OTHER PUBLICATIONS

International Search Report and Written Opinion from related PCT Application PCT/US 2009/004298, dated Dec. 21, 2009 (15 pgs).

(Continued)

*Primary Examiner* — T. Victor Oh
(74) *Attorney, Agent, or Firm* — Brooks, Cameron & Huebsch, PLLC

(57) ABSTRACT

Processes and systems for purifying ethylene oxide, including introducing a feed stream including ethylene oxide to a heat exchanger to heat the feed stream, feeding the heated feed stream to a distillation apparatus base below a first stage, removing from the distillation apparatus an impurity fraction as a top exit stream from the distillation apparatus located at a top take-off on the distillation apparatus, removing from the distillation apparatus an ethylene oxide stream of 99.7 weight percent purity, based on the total weight of the ethylene oxide stream, from the distillation apparatus, and removing from the distillation apparatus an aldehyde enriched fraction as a bottom stream from the distillation apparatus, where the aldehyde enriched fraction is fed directly to a glycol reactor.

19 Claims, 3 Drawing Sheets

(56) References Cited

U.S. PATENT DOCUMENTS

| | | | |
|---|---|---|---|
| 2,771,473 A | 11/1956 | Courter | |
| 2,775,600 A | 12/1956 | Maslen | |
| 2,815,650 A | 12/1957 | McIntire et al. | |
| 3,094,401 A | 6/1963 | Lidell | |
| 3,165,539 A | 1/1965 | Lutz | |
| 3,174,262 A | 3/1965 | Lutz | |
| 3,216,177 A | 11/1965 | Bracken at al. | |
| 3,398,062 A | 8/1968 | Tsao | |
| 3,418,338 A | 12/1968 | Gilman et al. | |
| 3,531,376 A | 9/1970 | Minoda et al. | |
| 3,729,899 A | 5/1973 | Cunningham | |
| 3,745,092 A | 7/1973 | Vanderwater | |
| 3,766,714 A | 10/1973 | Cunningham et al. | |
| 3,867,113 A | 2/1975 | Foster et al. | |
| 3,904,656 A * | 9/1975 | Broz | 549/538 |
| 3,948,621 A | 4/1976 | Cocuzza et al. | |
| 3,964,980 A | 6/1976 | Ozero | |
| 4,033,617 A | 7/1977 | Cocuzza et al. | |
| 4,134,797 A | 1/1979 | Ozero | |
| 4,597,833 A | 7/1986 | N'eel et al. | |
| 4,845,296 A | 7/1989 | Ahmed et al. | |
| 4,966,657 A | 10/1990 | Delannoy et al. | |
| 4,983,260 A | 1/1991 | N'eel et al. | |
| 5,233,060 A | 8/1993 | Pendergast et al. | |
| 5,529,667 A | 6/1996 | Coffey | |
| 6,080,897 A | 6/2000 | Kawabe | |
| 6,123,812 A | 9/2000 | Bessling et al. | |
| 6,437,199 B1 | 8/2002 | Oka et al. | |
| 6,498,272 B1 | 12/2002 | Schröder et al. | |
| 6,833,057 B1 | 12/2004 | Bessling et al. | |
| 7,179,875 B2 | 2/2007 | Fuchs et al. | |
| 2004/0236049 A1 | 11/2004 | Fuchs et al. | |
| 2005/0103617 A1 | 5/2005 | Andreis et al. | |
| 2005/0277778 A1 | 12/2005 | Viswanathan et al. | |
| 2006/0264648 A1 | 11/2006 | Beekman et al. | |

FOREIGN PATENT DOCUMENTS

| | | |
|---|---|---|
| DE | 199 24 533 | 11/2000 |
| DE | 19924533 | 11/2000 |
| DE | 101 38 150 | 2/2003 |
| DE | 10138150 | 2/2003 |
| EP | 0 181 273 | 5/1986 |
| EP | 0181273 | 5/1986 |
| FR | 1 330 900 | 5/1963 |
| FR | 1330900 | 5/1963 |
| FR | 2 851 564 | 8/2004 |
| FR | 2851564 | 8/2004 |
| GB | 564646 | 10/1944 |
| GB | 589547 | 6/1947 |
| JP | 54-16416 | 2/1979 |
| JP | 54016416 | 2/1979 |
| JP | 62-12770 | 1/1987 |
| JP | 62012770 | 1/1987 |
| WO | WO 03/055869 | 7/2003 |
| WO | WO 2004/056453 | 7/2004 |
| WO | WO 2006/120207 | 11/2006 |
| WO | WO 2009/094103 | 7/2009 |
| WO | WO 2009/105252 | 8/2009 |

OTHER PUBLICATIONS

Viera, G.A., et al. "Lessons Learned from the Ethylene Oxide Explosion at Seadrift, Texas". Chem Eng. Progess. 89 (8), pp. 66-75 (1993).

Wankat, P.C. et al. "Two-Feed Distillation: Same-Composition Feeds with Different Enthalpies" Ind. Eng. Chem. Res. 1993, 32, 3061-3067.

Cleveland et al. "Meteor Revolution" Hydrocarbon Engineering Oct. 2001 pp. 69-71.

Xiangyu, Z. "A Comparison of EO/EG Process Technologies" Sinopec Shanghai Engineering Co. Shanghai, 2006.

International Search Report and Written Opinion from related PCT Application PCT/US2009/004298, dated Dec. 21, 2009 (15 pgs).

"U.S. Appl. No. 12/460,810, Notice of Allowance mailed Dec. 7, 2011", 12 pages.

"U.S. Appl. No. 12/460,756, Non Final office action mailed Dec. 5, 2011", 15 pages.

"U.S. Appl. No. 12/460,755, Non Final office action mailed Dec. 6, 2011", 11 pages.

"U.S. Appl. No. 12/460,756, Response filed Mar. 5, 2012 for Non Final office action mailed Dec. 5, 2011", 10 pages.

"U.S. Appl. No. 12/460,755, Response filed Mar. 5, 2012 for Non Final office action mailed Dec. 6, 2011", 7 pages.

"U.S. Appl. No. 12/460,775, Notice of Allowance mailed Jun. 8, 2011", 5 pages.

"U.S. Appl. No. 12/460,775, Notice of Allowance mailed Jul. 13, 2011", 5 pages.

* cited by examiner

ALKYLENE OXIDE PURIFICATION PROCESSES AND SYSTEMS

This application claims priority to U.S. Provisional Application 61/137,514 filed Jul. 31, 2008, the specification of which is incorporated herein by reference, and is co-filed with co-owned U.S. Patent Applications: Ser. No. 61/137,494, entitled "Alkylene Oxide Recovery Systems" filed on Jul. 31, 2008; Ser. No. 61/137,517, entitled "Alkylene Oxide Recovery Systems" filed on Jul. 31, 2008; Ser. No. 61/137,493, entitled "Alkylene Oxide Purification Processes and Systems" filed on Jul. 31, 2008; and Ser. No. 61/137,485, entitled "Alkylene Oxide Purification Systems" filed on Jul. 31, 2008.

FIELD OF THE DISCLOSURE

This disclosure relates to a process for distilling alkylene oxide from feed streams containing the same. More particularly, this disclosure relates to an improved process for distilling ethylene oxide from an impure feed stream further containing aldehyde impurities.

BACKGROUND

Ethylene oxide is manufactured worldwide in amounts of several million tons per year. It can be prepared in large quantities by oxidizing ethylene with air or pure oxygen over a suitable catalyst, for example a silver-containing catalyst, at elevated temperature (e.g., one hundred (100) degrees Celsius (° C.) to five hundred (500)° C.) and at superatmospheric pressure (e.g., two (2) to twenty-five (25) atmospheres (atms)) whereby ethylene and oxygen react to form ethylene oxide.

The ethylene oxide production reactor effluent, which can include ethylene oxide, unconverted ethylene and oxygen, carbon dioxide, aldehydes, other low molecular weight hydrocarbons, and fixed gases such as argon and nitrogen, can be treated with water to remove the ethylene oxide. The ethylene oxide can then be further refined into a form with sufficient purity for industrial applications from the resulting mixture of ethylene oxide and water.

SUMMARY

Embodiments of the present disclosure provide processes and systems for distilling alkylene oxide from a feed stream containing the alkylene oxide. Embodiments are adaptable to commercial scale alkylene oxide production. While the embodiments herein provide for processes and systems for distilling alkylene oxide from a feed stream containing the alkylene oxide, a representative example of ethylene oxide will be discussed herein. It is appreciated, however, that the processes and systems provided herein may be useful for distilling other alkylene oxides.

For the various embodiments, the process for distilling ethylene oxide includes removing from a distillation apparatus an impurity fraction as a top exit stream located at a top take-off on the distillation apparatus; removing from the distillation apparatus an ethylene oxide stream of at least 99.7 weight percent purity, based on the total weight of the ethylene oxide stream; and removing from the distillation apparatus an aldehyde enriched fraction as a bottom stream.

For the various embodiments, the process can also include distilling the feed stream including ethylene oxide in the distillation apparatus to produce the impurity fraction and the aldehyde enriched fraction, where the aldehyde enriched fraction includes, ethylene oxide in a range of about seven (7) percent to about twenty (20) percent by weight and water in a range of about eighty (80) percent to about ninety-three (93) percent by weight, based on total weight of the aldehyde enriched fraction; and feeding the aldehyde enriched fraction without further processing to a glycol reactor. For the various embodiments, distilling the feed stream can produce an ethylene oxide stream of at least 99.7 weight percent purity.

For the various embodiments, the process can include introducing the feed stream including the ethylene oxide into the heat exchanger to heat the feed stream; and feeding the heated feed stream below a first separation stage of the distillation apparatus. In various embodiments, the process can also include heating a liquid content of the distillation apparatus in situ below the first separation stage of the distillation apparatus. For the various embodiments, it is possible to use a combination of the heat exchanger and the in situ heating below the first separation stage of the distillation apparatus in the process.

For the various embodiments, the heat exchanger and the distillation apparatus can be used in a system to distill ethylene oxide, where the system includes the heat exchanger and the distillation apparatus operably connected to the heat exchanger, where the heat exchanger heats the feed stream that enters the base of the distillation apparatus below the first separation stage of the distillation apparatus, and where the distillation apparatus includes a top exit stream, a side take-off located between a top and a bottom of the distillation apparatus, where the ethylene oxide stream is removed as a side stream at the side take-off, and a bottom exit stream, where the bottom exit stream is in direct connection with a glycol reactor.

DEFINITIONS

As used herein, "distilling" and a "distillation process" refer to a process of separating compounds based on their differences in volatilities by vaporization and subsequent condensation, as for purification or concentration. In embodiments discussed herein, distillation can be performed on an aqueous mixture to purify, recover, and/or separate ethylene oxide, where the "aqueous mixture" can be defined as a mixture of ethylene oxide, water, and other compounds in liquid form. As used herein, the terms "distill," "recover," "purify," and "separate" should be understood to refer to the distillation process as it is described herein.

As used herein, a "distillation apparatus" refers to a device that carries out the distillation process. The distillation apparatus, or column, as discussed herein, can have a diameter ranging from, for example, sixty-five (65) centimeters (cm) to six (6) meters (m) and have a height ranging from, for example, six (6) to sixty (60) m or more. As used herein, a "heat exchanger" refers to a device built for efficient heat transfer from one fluid to another whether the fluids are separated by a solid wall so that they never mix, or the fluids are directly contacted.

As used herein, "sensible heat" refers to the heat absorbed or evolved by a substance during a change of temperature that is not accompanied by a change of state. Thus, a "sensible heat heat exchanger" refers to a heat exchanger that transfers heat from one fluid to another without changing the state of the heating fluid.

As used herein, "latent heat" refers to an amount of energy released or absorbed by a substance during a change of state, such as during the condensation of steam. Thus, a "latent heat heat exchanger" refers to a heat exchanger that transfers heat from one fluid to another during a change of state of the heating fluid (e.g., steam).

In operations where a substance is to be separated into components, the liquid and the vapor phases of the substance can be brought into intimate contact by means of a distillation apparatus having at least one separation stage. A variety of such distillation apparatuses for making this separation are possible. These include tray towers, which include trays or plates (referred to herein as a "tray" or "trays") that provide the separation stages, and packed towers, which include packing (random and/or regular packing) that facilitates the separation stages. As appreciated, packed towers operate in a manner that is different than tray towers in that the liquid and vapor phases are in contact continuously in their path through the packed tower, rather than intermittently as is the case with tray towers. Thus, in a packed tower the liquid and gas compositions change continuously with height of packing.

As used herein a "separation stage" is defined as a volume, device or combination of devices in a distillation apparatus within or at which phases are brought into intimate contact, where mass transfer occurs between the phases tending to bring them to equilibrium, and where the phases can then mechanically separated. For the various embodiments, each tray of a tray tower and/or packing of a packed tower having a height equivalent to a theoretical plate ("HETP") is a separation stage, as these are the locations where fluids are brought into intimate contact, interphase diffusion occurs, and the fluids are separated. As such, the number of trays in a distillation apparatus can also be attributed to an equivalent number of separation stages that are obtained by using packing. For the various embodiments, the terms separation stage, tray and/or packing having a HETP can be used interchangeably, unless otherwise stated to the contrary.

As appreciated by one skill in the art, determining a number of equilibrium stages (theoretical trays) for use in a distillation apparatus can be calculated based on the material balances and equilibrium considerations of the compounds (e.g., ethylene oxide, water, and other compounds in liquid form) to be separated in the substance (e.g., the aqueous mixture of the present disclosure). The efficiency of the separation stage, and therefore the number of separation stages that are actually used, can be determined by the mechanical design used and the condition of operation for the distillation apparatus. For the various embodiments provided herein, the number of equilibrium stages (or theoretical trays) could be used in place of the number of separation stages provided in the present disclosure through the use of the efficiency of the separation stage of the distillation apparatus.

As used herein, references to separation stage numbers are from the bottom of the distillation apparatus to the top of the distillation apparatus. So, a first separation stage is at or near the bottom of the distillation apparatus with subsequent separation stages being numbered progressively up the distillation apparatus (e.g., the second separation stage follows the first separation stage, the third separation stage follows the second, etc.).

As used herein, "a," "an," "the," "at least one," and "one or more" are used interchangeably. The terms "comprises" and variations thereof do not have a limiting meaning where these terms appear in the description and claims. Thus, for example, a stripping section located in an ethylene oxide recovery column to convert a portion of "a" feed stream to a gas phase portion can be interpreted to mean that the ethylene oxide recovery column includes "one or more" feed streams.

The term "and/or" means one, more than one, or all of the listed elements.

As used herein, the term "about" may not be limited to the precise value specified. In at least one instance, the variance indicated by the term "about" can be determined with reference to the precision of the measuring instrumentation.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION

Figure 1:
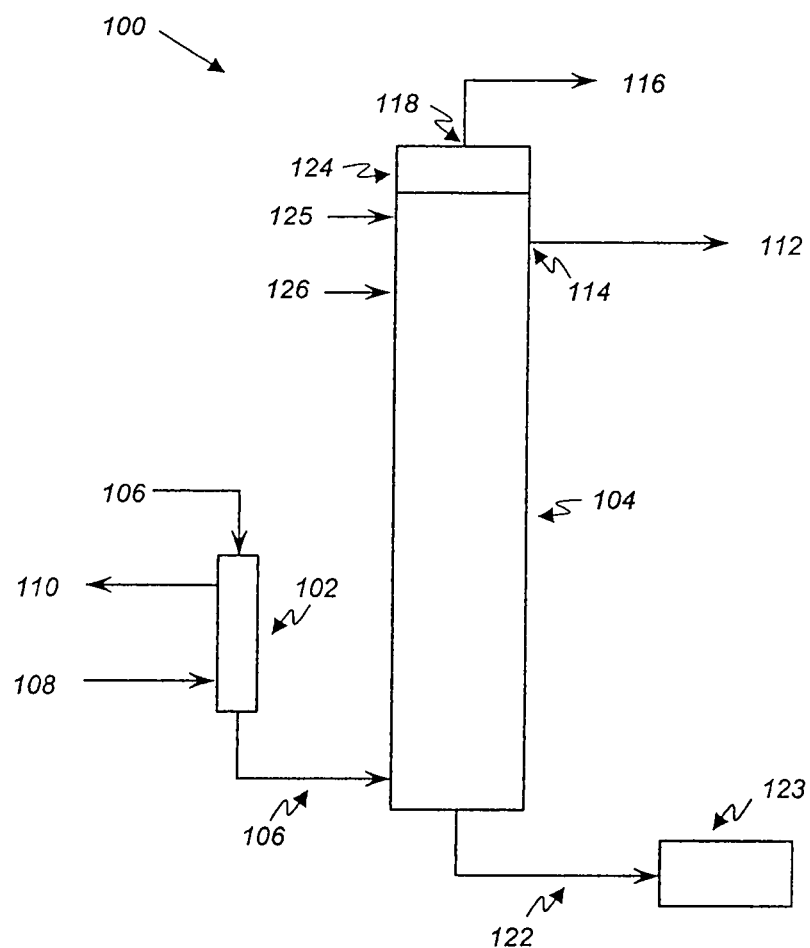
FIG. 1 provides an embodiment of a system of the present disclosure.

Embodiments of the present disclosure include processes and systems for distilling ethylene oxide from a feed stream. The system embodiments include a heat exchanger and a distillation apparatus operably connected to the heat exchanger. For the various embodiments, the heat exchanger can be a sensible heat heat exchanger, which transfers heat from one fluid to another without changing the state of the heating fluid. For the various embodiments, the heat exchanger can also be a latent heat heat exchanger, where the heating fluid can at least partially change phases during the heating process.

Embodiments of the present disclosure achieve separation of ethylene oxide and impurities in a single distillation apparatus utilizing an aqueous mixture as a feed stream, a heat exchanger that provides heat to the aqueous mixture and/or the liquid within the distillation apparatus without the use of an external reboiler and/or external circulating loop containing ethylene oxide, and operating the distillation apparatus such that an aldehyde enriched fraction bottom stream is produced that can be fed directly to a glycol reactor. The use of a single distillation apparatus can, in some embodiments, result in lower equipment cost when building a system as described herein, as compared to systems having two or three distillation apparatuses for purifying ethylene oxide. In some embodiments, pure ethylene oxide can be taken off the distillation apparatus as a side stream; by doing so, light impurities, such as carbon dioxide, oxygen, nitrogen, and argon, among others, can be taken off the distillation apparatus as a top stream.

Several steps can be performed to obtain the aqueous mixture that is used as the feed stream to the distillation apparatus. As described herein, the steps to produce ethylene oxide and to use the produced ethylene oxide in further reactions occur in one place, for example, in an ethylene oxide processing plant. The various steps, however, can also occur in separate facilities.

In addition, in an ethylene oxide production unit, the ethylene oxide production processes can be interlinked with ethylene oxide recovery processes. In certain cases where the ethylene oxide production unit is operated along with downstream product manufacturing units such as, for example an ethylene glycol manufacturing unit, the ethylene oxide processes can also be interlinked with ethylene glycol manufacturing processes to maximize energy utilization, which in turn can lower production costs.

Alkylenes (olefins) employed in the process of this disclosure can be characterized by the following structural formula (I):

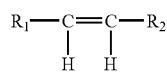

wherein $R_1$ and $R_2$ are each individually selected from hydrogen and lower monovalent radicals, preferably $C_1$-$C_6$ alkyl radicals including methyl, ethyl, propyl, butyl, and higher homologues having up to six carbon atoms. Preferably, $R_1$ and $R_2$ are each individually selected from hydrogen, methyl, and ethyl. More preferably, each $R_1$ and $R_2$ is hydrogen, and the preferred olefin is ethylene. The corresponding alkylene oxides produced in the process of this disclosure are preferably characterized by the following structural formula (II):

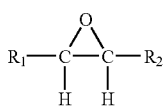

wherein $R_1$ and $R_2$ are identified herein in connection with the reactant olefin. Most preferably, the alkylene oxide is ethylene oxide (i.e., $R_1$ and $R_2$ are both hydrogen).

Oxygen may be provided to the process as pure molecular oxygen. Alternatively, oxygen may be provided as an oxygen-containing gas, where the gas further contains one or more gaseous components, for example, gaseous diluents such as nitrogen, helium, methane, and argon, which are essentially inert with respect to the oxidation process. In some embodiments, a suitable oxygen-containing gas is air. Additionally, the oxygen-containing gas may contain one or more of the following gaseous components: water, carbon dioxide, and various gaseous promoters and/or gaseous by-product inhibitors, as discussed herein.

The relative volumetric ratio of alkylene to oxygen in the feed stock gas may range in accordance with known values. Typically, the volumetric ratio of alkylene to oxygen in the feed stock may vary from about 2:1 to about 6:1. Likewise, the quantity of inert gases, diluents, or other gaseous components such as water, carbon dioxide, and gaseous promoters and gaseous by-product inhibitors, may vary in accordance with known ranges as found in the art.

The present disclosure is applicable to epoxidation reactions in a suitable reactor, for example, fixed bed reactors, fixed bed tubular reactors, continuous stirred tank reactors (CSTRs), and fluid bed reactors, a wide variety of which are known in the art. The desirability of recycling unreacted feed, employing a single-pass system, or using successive reactions to increase ethylene conversion by employing reactors in a series arrangement can also be readily determined by those skilled in the art.

The particular mode of operations selected can be dictated by process economics. Conversion of alkylene (olefin), preferably ethylene, to alkylene oxide, preferably ethylene oxide, can be carried out, for example, by continuously introducing a feed stream containing alkylene (e.g., ethylene) and oxygen, or an oxygen-containing gas, to a catalyst-containing reactor at a temperature of from about two hundred (200) degrees Celsius (° C.) to about three hundred (300)° C., and a pressure which may be in a range of from about five (5) atmospheres (five hundred six (506) kilopascals (kPa)) to about thirty (30) atmospheres (3,040 kPa), depending on the mass velocity and productivity desired. Residence times in large scale reactors can be on the order of about 0.1 to about five (5) seconds. In some embodiments, the feedstock can be passed over a catalyst in the reactor, for example, a silver-containing catalyst. The resulting alkylene oxide, preferably ethylene oxide, can then be separated and recovered from the reaction products using further processes.

As discussed herein, embodiments of the present disclosure include distilling alkylene oxide from a feed stream. While the embodiments herein provide for processes and systems for distilling alkylene oxide from a feed stream containing the alkylene oxide, a representative example of ethylene oxide will be discussed herein. However, one of skill in the art will appreciate that embodiments of the present disclosure may also apply to other alkylene oxides including propylene oxide, butylene oxide, methylene oxide, among others.

In nearly all processes containing ethylene oxide and water, some degree of reaction between ethylene oxide and water to form ethylene glycol can occur. The reactivity is highest in systems with higher temperatures and longer residence times. In most cases, the formation of ethylene glycol in the ethylene oxide purification column/equipment is not ideal as the reaction conditions are not ideal and the formation of monoethylene glycol (MEG) can lead to further side reactions. For instance, MEG can react with additional ethylene oxide to form higher glycols, such as diethylene glycol and triethylene glycol, or glycols can be oxygenated to form the resulting glycol aldehyde with each side reaction resulting in lower overall process efficiency to MEG. Monoethylene glycol can be produced from ethylene via the intermediate ethylene oxide, where ethylene oxide reacts with water to produce MEG in a glycol reactor, as discussed herein. High selectivity to MEG is desirable since MEG is an important raw material for industrial applications, including the use of MEG in the manufacture of polyester resins, films, and fibers. In addition, MEG is important in the production of anti-freezes, coolants, aircraft anti-icers and deicers, and solvents.

Ethylene glycol can be produced by the (catalyzed or uncatalyzed) hydrolysis of ethylene oxide. Ethylene oxide hydrolysis can proceed with either acid or base catalysis or uncatalyzed in neutral medium. Acid catalyzed hydrolysis activates the ethylene oxide by protonation for the reaction with water. Base catalyzed hydrolysis, however, results in considerably lower selectivity to ethylene glycol, producing diethylene glycol and higher glycols (e.g., triethylene and tetraethylene glycols) in addition to the ethylene glycol. Ethylene glycol monoethers can be manufactured by the reaction of an alcohol with ethylene oxide. Also, ethanolamine can be manufactured by the reaction of ethylene oxide with ammonia. See, for example, U.S. Pat. No. 4,845,296.

In some instances, to produce ethylene oxide, a feedstock of ethylene and pure oxygen, or air, after blending with cycle gas, can enter an ethylene oxide reactor, along with other compounds. The ethylene oxide reactor can be a fixed bed reactor or a fluid-bed reactor, as discussed herein. In some embodiments, a ballast gas (e.g., methane, nitrogen) can be added to the feed stock gas to increase the lower flammability limit of the inlet gas, enhancing the safety and stability of the system. In addition, in some embodiments, a small quantity of ethylene dichloride or other chlorine-containing compounds can be introduced into the feed stock gas to decrease side reactions and to improve the selectivity of ethylene oxidization.

In some embodiments, the per-pass conversion of ethylene to ethylene oxide can be low (i.e., on the order of one (1) percent or less). The gaseous reaction effluent thus formed contains dilute concentrations of ethylene oxide along with unreacted ethylene and oxygen, aldehydes, acid impurities, nitrogen, and argon, among other components. In some embodiments, the aldehydes can include formaldehyde and acetaldehyde. In some embodiments, the per-pass conversion of ethylene to ethylene oxide can range from five (5) percent to twenty-five (25) percent.

The ethylene oxide can be separated and recovered from the gaseous reaction effluent. For example, the gaseous reaction effluent from the reactor can be scrubbed with an absorbent, such as water, to form an aqueous mixture containing ethylene oxide in an absorber column. The absorption of ethylene oxide in water can recover ethylene oxide from unreacted ethylene, oxygen, and/or other gaseous components (e.g., carbon dioxide, nitrogen, argon). The remaining gaseous materials can then be recycled as cycle gas to be mixed with the feedstock of ethylene and pure oxygen, and fed to the ethylene oxide reactor for the production of ethylene oxide as gaseous reaction effluent.

The aqueous mixture containing ethylene oxide from the absorber column can then be passed to a stripper (e.g., a stripping column) where steam is introduced to remove ethylene oxide product as overhead. The overhead product from the stripper, containing carbon dioxide, ethylene oxide, gaseous inerts, and water vapor, can then be cooled to partially condense the ethylene oxide and water, and the resulting mixture of vapor and liquid or just vapor can be passed to an ethylene oxide reabsorber, in which the uncondensed ethylene oxide vapor is reabsorbed in water. From the reabsorption step, an aqueous mixture can be obtained which contains reabsorbed ethylene oxide and aldehydic impurities, such as formaldehyde and acetaldehyde, as well as dissolved carbon dioxide and other gaseous impurities. This aqueous mixture is then further purified using the aqueous mixture as the feed stream in embodiments of the present disclosure to provide ethylene oxide of appropriate purity for industrial use.

In the Figures herein, as will be appreciated, elements shown in the embodiment herein can be added, exchanged, and/or eliminated so as to provide any number of additional embodiments of processes and/or systems. In addition, as will be appreciated, the proportion and the relative scale of the elements provided in the figures is intended to illustrate the embodiments of the present invention, and should not be taken in a limiting sense.

The Figures herein follow a numbering convention in which the first digit or digits correspond to the drawing Figure number and the remaining digits identify an element or component in the drawing. Similar elements or components between different figures may be identified by the use of similar digits. For example, 110 may reference element "10" in FIG. 1, and a similar element may be referenced as 210 in FIG. 2. In addition, the description herein of an element and/or component provided for one or more Figures is applicable to and associated with other Figures illustrating the same element and/or component number but which do not necessarily provide the express description thereof. So, for example, when element "10" in FIG. 1 is expressly discussed herein this express discussion is also applicable to element "10" in the other Figs. where it may appear.

FIG. 1 provides an embodiment of a system 100 according to the present disclosure. As shown in the embodiment of FIG. 1, the system 100 can include a heat exchanger 102 and a distillation apparatus 104. As discussed herein, embodiments of the present disclosure can be used to purify the aqueous mixture of ethylene oxide produced from the reabsorption step, referred to hereinafter as the feed stream, as discussed herein. Examples of possible compounds in addition to water and ethylene oxide in the feed stream include ethylene glycol, oligo(ethylene glycol)s, aldehydes, such as formaldehyde and/or acetaldehyde, carbon dioxide, and methane, among other compounds.

In some embodiments, the feed stream to be distilled includes, in each case based on its weight, from about five (5) to about ninety-five (95) percent by weight, preferably from about five (5) to about fifty (50) percent by weight, and more preferably about five (5) to about twenty (20) percent by weight ethylene oxide and from about ninety-five (95) to about five (5) percent by weight, preferably from about ninety-five (95) to about fifty (50) percent by weight, and more preferably about ninety-five (95) to about eighty (80) percent by weight of water. The feed stream can further include aldehydes in a range of about one (1) to about one hundred (100) parts per million (ppm) by weight. It will be appreciated that the sum of the ingredients of the aqueous mixture is one hundred (100) percent in each case.

For the various embodiments, the feed stream 106 produced from adsorbing the dilute ethylene oxide mixture in the absorber, stripper, and subsequent reabsorber can be introduced to the heat exchanger 102 to heat the feed stream 106. The heat exchanger 102 can allow for the integration of low energy, or low temperature, streams into the process. By using the heat exchanger 102 to heat the low temperature feed stream 106 before it is fed into the distillation apparatus 104, less energy can be input to the distillation apparatus 104 to heat the feed stream 106 to the boiling point, and thus, distill ethylene oxide from the feed stream 106, saving energy overall, as compared to a process that does not include a heat exchanger 102 before a distillation apparatus 104, as discussed herein. In some embodiments, the heat exchanger 102 can be a predominantly sensible heat heat exchanger, for example, a shell and tube heat exchanger or a plate heat exchanger.

In additional embodiments, the heat exchanger 102 can be a latent heat heat exchanger, as discussed herein, where low pressure steam can be used as the heating fluid. As used herein, the low pressure steam can be supplied at a temperature that is incrementally higher than the feed stream 106 entering the heat exchanger 102. For the various embodiments, the incrementally higher temperature of the low pressure steam can be about 5 to 10° C. higher than the feed stream 106 entering the heat exchanger 102. Examples of low pressure steam values can include, but are not limited to, 1-500 psia (pounds-force per square inch absolute), with 5-50 psia and/or 10-30 psia condensing pressures being suitable value ranges.

In some embodiments, the use of a sensible heat heat exchanger, as defined herein, can allow heat to be added to the feed stream 106 while limiting the maximum temperature that the feed stream 106 can reach to the temperature of the liquid used on the heat input side of the heat exchanger. The use of a sensible heat heat exchanger can also reduce the use of high pressure steam, as compared to a low pressure steam as provided herein, as the heating medium in the heat exchanger 102. Reducing the use of high pressure steam can increase the safety of heating the ethylene oxide-containing feed stream 106 since ethylene oxide is a reactive compound with a low decomposition temperature. The use of a sensible heat heat exchanger can also allow for energy integration between the heat exchanger 102 and other areas in an ethylene oxide processing plant where heat is in excess, by routing an excess hot stream to the heat exchanger 102 to heat the feed stream 106, and subsequently cool the excess hot stream.

In various embodiments using a shell and tube heat exchanger, the heat exchanger 102 can be operated using counter-flow, using a heat exchange fluid 108 (e.g., water) entering the heat exchanger 102 at a high temperature at the bottom of the heat exchanger 102. As the fluid 108 flow heats the feed stream 106, energy is transferred from the fluid 108 to the feed stream 106, in effect cooling the fluid 108. The cooled heat exchange fluid 110, in some embodiments, can exit the heat exchanger 102 from the side of the heat exchanger 102 at the top, as shown in FIG. 1. In some embodiments, the heat exchanger 102 can be operated using a parallel flow.

Although the heat exchanger 102 is illustrated in FIG. 1 showing the feed stream 106 entering the top of the heat exchanger 102 and flowing down the heat exchanger 102, the feed stream 106 can also flow through the heat exchanger 102 from the bottom to the top. The heat exchange fluid 108 entrance and exit points can be correspondingly modified to heat the feed stream 106. Other heat exchanger 102 arrangements are also possible.

In some embodiments, the feed stream 106 entering the distillation apparatus 104 is at a predetermined temperature or in a predetermined temperature range, where the predetermined temperature is chosen based on the boiling point of the feed stream. For example, the feed stream 106 can enter the distillation apparatus 104 at a temperature in a range of about one hundred (100) to about one hundred twenty (120)° C. In some embodiments, the heat exchanger 102 can be operated to heat the feed stream 106 to the predetermined temperature or predetermined temperature range. For example, the heat exchanger 102 can be operated to heat the feed stream 106 entering the heat exchanger 102 at a temperature in a range of about fifty (50)° C. to about sixty (60)° C. to the predetermined temperature range of, for example, about one hundred (100)° C. to about one hundred twenty (120)° C. By heating the feed stream 106 prior to the feed stream 106 entering the distillation apparatus 104, less energy is spent heating the feed stream 106 inside the distillation apparatus 104. As appreciated by one skilled in the art, different operating parameters of the heat exchanger 102 can be varied to heat the feed stream 106 to the predetermined temperature, including the type of heat exchange fluid 108, the flow rate of the heat exchange fluid 108, and/or the inlet temperature of the heat exchange fluid 108, among others. Once the feed stream 106 is passed through the heat exchanger 102, it can be fed to the distillation apparatus 104.

In some embodiments, the predetermined temperature or predetermined temperature range of the feed stream 106 entering the distillation apparatus 104 can be chosen to give a desired amount of boil-up in the distillation apparatus 104. The boil-up in the distillation apparatus 104 is a combination of vapor for reflux, vapor of ethylene oxide to be removed, for example, as a side stream at a side take-off, and the vapor of light impurities to be removed at the top of the distillation apparatus 104, as discussed further herein.

Figure 2:
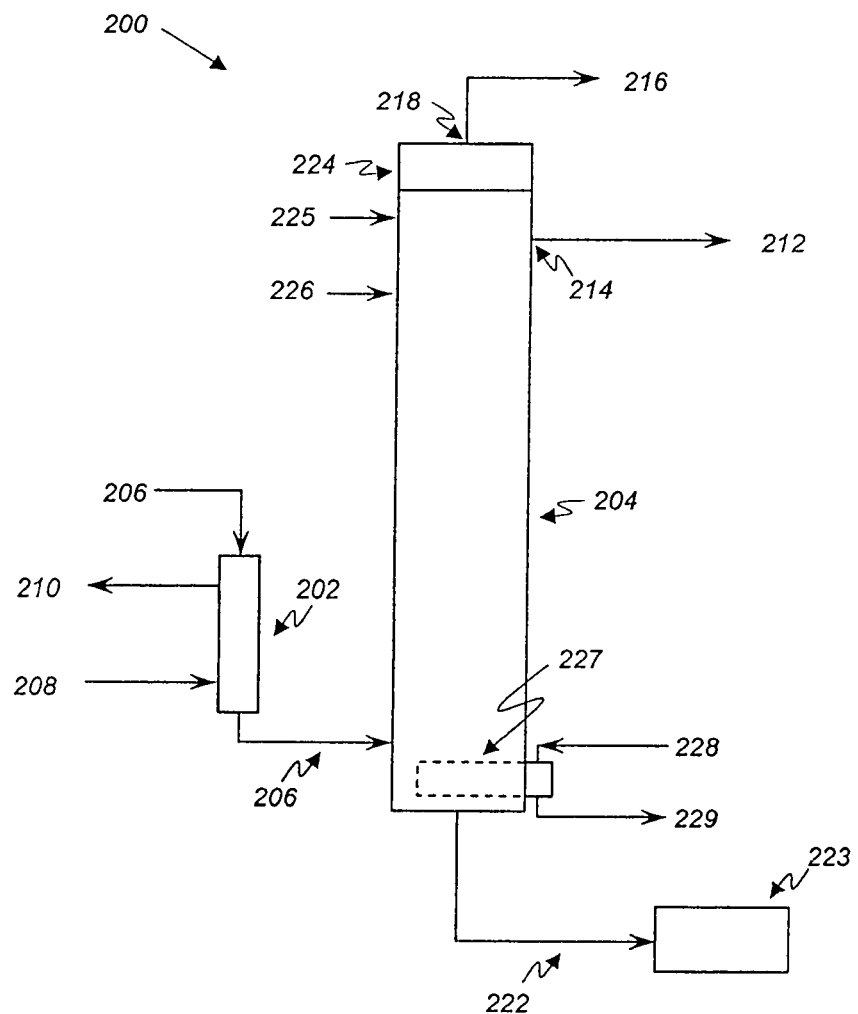
FIG. 2 provides an embodiment of a system of the present disclosure.

FIG. 2 provides an additional embodiment of the system 200 of the present disclosure. The system 200 illustrated in FIG. 2 includes the same structures as are described herein for the system 100, with the addition of an insertion type reboiler 227. For the various embodiments, the insertion type reboiler 227 can be a heat exchanger, as provided herein, where heat exchange fluid 228 (e.g., water) enters at a high temperature, heats the liquid content of the distillation apparatus 200 and the cooled heat exchange fluid 229 exits the insertion type reboiler 227.

As illustrated, the insertion type reboiler 227 can be positioned in situ below a first separation stage of distillation apparatus 204, where it can be used to provide heat to at least partially vaporize (e.g., provide boil-up) the liquid in the bottom of the distillation apparatus 204. For the various embodiments, the insertion type reboiler 227 can be positioned below the bottom liquid level of the distillation apparatus 204 to vaporize liquid to generate column vapor for good vapor/liquid contacting and multistage separation. Providing boil-up in this manner is in contrast to diverting the liquid from the bottom of the distillation apparatus 204 to an external reboiler, via a recirculation loop, the use of which may raise safety concerns due to the presence of ethylene oxide in the diverted liquid stream. For the various embodiments, using an insertion type reboiler 227, instead of a typical external circulating loop and reboiler containing ethylene oxide, can help to increase the inherent safety of the system 200 by reducing the inventory of ethylene oxide outside the distillation apparatus 204 and can help to reduce the opportunity for ethylene oxide to be exposed to high temperature heating medium if the circulation loop would fail to operate properly.

For the various embodiments, the insertion type reboiler 227 can utilize latent heat or sensible heat in heating the liquid content of the distillation apparatus 204. As illustrated, the heat exchange fluid can enter the top of the insertion type reboiler 227 when latent heat transfer is being used. In an additional embodiment, the heat exchange fluid can enter either the top or the bottom of the insertion type reboiler 227 when sensible heat transfer. For the various embodiments, it is also possible to use both the heat exchanger 202 and the insertion type reboiler 227 to provide the boil-up in the distillation apparatus 204. For the various embodiments, it is possible to operate the system 200 with the insertion type reboiler 227 as the only source of heat for the distillation apparatus 204 boil-up. For the various embodiments, the use of the insertion type reboiler 227 as the only source of heat for the distillation apparatus 204 boil-up might be due to a greater need for heat than can be, or is desired to be, transferred in the heat exchanger 202.

Figure 3:
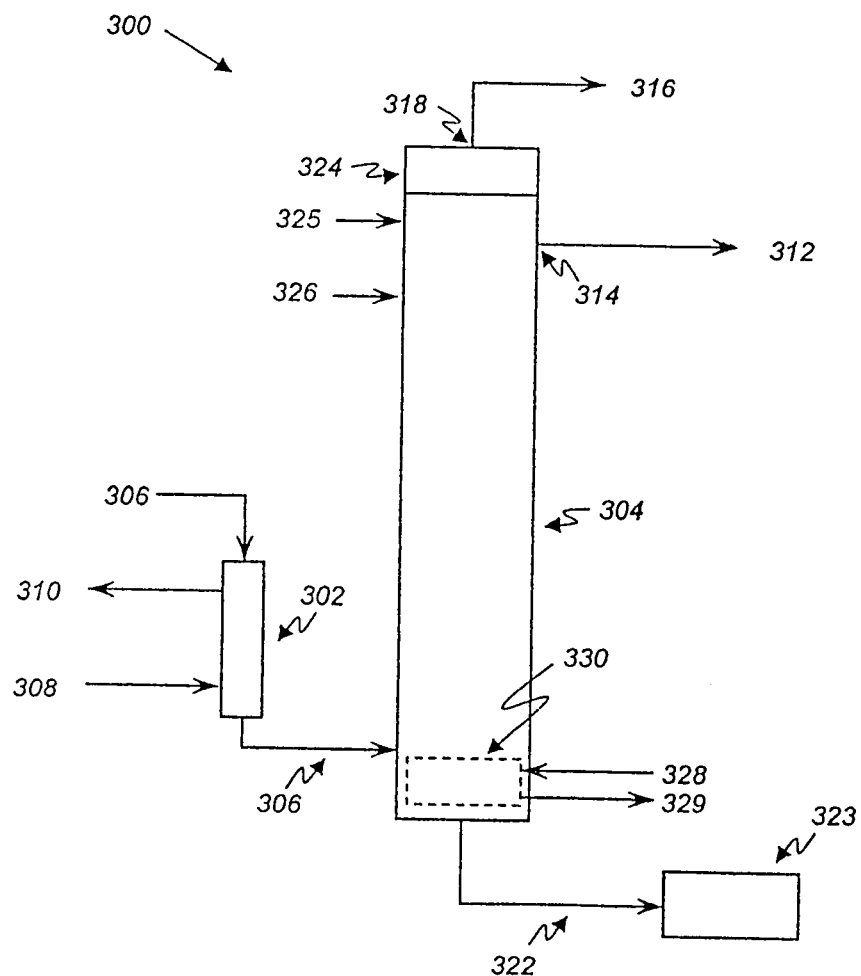
FIG. 3 provides an embodiment of a system of the present disclosure.

FIG. 3 provides an additional embodiment of the system 300 of the present disclosure. The system 300 illustrated in FIG. 3 includes the same structures as are described herein for the system 100, with the addition of an internal reboiler 330. For the various embodiments, the internal reboiler 330 can be a heat exchanger, as provided herein, where heat exchange fluid 328 (e.g., water) enters at a high temperature, heats the liquid content of the distillation apparatus 300 and the cooled heat exchange fluid 329 exits the internal reboiler 330.

As illustrated, the internal reboiler 330 can be positioned in situ below a first separation stage of distillation apparatus 304, where it can be used to provide heat to at least partially vaporize (e.g., provide boil-up) the liquid in the bottom of the distillation apparatus 304. For the various embodiments, the internal reboiler 330 can be positioned below the bottom liquid level of the distillation apparatus 304 to vaporize liquid to generate column vapor for good vapor/liquid contacting and multistage separation. Providing boil-up in this manner is in contrast to diverting the liquid from the bottom of the distillation apparatus 304 to an external reboiler, via a recirculation loop, the use of which may raise safety concerns, as previous discussed herein, due to the presence of ethylene oxide in the diverted liquid stream.

For the various embodiments, the internal reboiler 330 can utilize latent heat or sensible heat in heating the liquid content of the distillation apparatus 304. As illustrated, the heat exchange fluid can enter the top of the internal reboiler 330 when latent heat transfer is being used. In an additional embodiment, the heat exchange fluid can enter either the top or the bottom of the internal reboiler 330 when sensible heat transfer. For the various embodiments, it is also possible to use both the heat exchanger 302 and the internal reboiler 330 to provide the boil-up in the distillation apparatus 304. For the various embodiments, it is possible to operate the system 300 with the internal reboiler 330 as the only source of heat for the distillation apparatus 304 boil-up.

Referring again to FIG. 1, the operating conditions within the distillation apparatus 104 can be adjusted according to processing conditions. In various embodiments, the distillation apparatus 104 can be operated at atmospheric pressure. In some embodiments, the distillation apparatus 104 can be operated slightly above atmospheric pressure to reduce the heat requirements in the distillation apparatus 104. In certain embodiments, there may be a gradient in pressure across the distillation apparatus 104, and this gradient may be a gradual change across the distillation apparatus 104 and/or various sections of the distillation apparatus 104, or may be an abrupt pressure change.

Although embodiments of the present disclosure are not limited to a distillation apparatus 104 of a certain height, the distillation apparatus 104 can include enough separation stages to distill the feed stream 106 entering the distillation apparatus 104.

As will be appreciated by one skilled in the art, the design and/or operation of the distillation apparatus 104, the heat exchanger 102, the insertion type reboiler 227 and/or the internal reboiler 330 can depend on the composition of the feed stream 106 as well as the composition of the desired products, among other things. In some instances, for example, with a binary component feed, analytical methods such as the McCabe Thiele method or the Fenske equation can be used to determine the number of equilibrium stages to use to achieve the desired separation. For a multi-component feed stream, simulation models can be used for both design (e.g., to determine the number of equilibrium stages needed in order to achieve the desired separation) and operation (e.g., to determine the optimum operating conditions). In addition, once the number of equilibrium stages is determined, one skilled in the art can use experimentation to determine the number of separation stages (e.g., the actual number of trays or height of packing) to use in a column to achieve the desired separation.

The distillation apparatus 104 of the present disclosure can be operated with distillation trays (plates), packing, or a combination of distillation trays and packing. The distillation trays can be of the type of plates found in distillation columns, such as sieve plates, bubble-cap plates or valve plates, among others. In some embodiments, the distance between each tray can vary. In addition, in embodiments using packing, the packing material can be random dumped packing such as, for example, Raschig rings, Pall rings, or Bialecki rings in metal or ceramic. The packing material can also be structured sheet-metal packing such as those known and commercially available for example under the designations Gempak® (Kock-Glitsch, LP, Dallas, Tex., U.S.A) and/or Mellapak® (Gebr. Sulzer, Winterthur, Switzerland).

In embodiments where random packing is employed, the total required height of packing to provide the required number of separation stages can be determined by multiplying the number of calculated equilibrium stages by the Height Equivalent to a Theoretical Plate, or HETP. The HETP is a value of the height of packing that will give the same separation as an equilibrium stage. As known to one skilled in the art, the HETP can vary depending on the type of packing selected.

In some embodiments, the total height of packing can be split into one or more zones with vapor-liquid redistributors in between the zones, for example, to accommodate height limitations due to packing structural integrity or to accommodate feed streams or product streams. In some embodiments, packing may offer the advantage of a lower pressure drop as compared to trays, although consideration must also be given to the cost difference arising from the choice of trays versus packing.

In embodiments where the distillation apparatus 104 has trays (i.e., a tray tower), the trays can be physical devices which are used to provide contact between an upflowing vapor and a downflowing liquid inside the distillation apparatus 104. In some instances, the efficiency of a tray can be lower than that of a theoretical one hundred (100) percent efficient equilibrium stage, hence, the distillation apparatus 104 can have more actual, physical trays (separation stages) than the required number of theoretical vapor-liquid equilibrium stages.

In some embodiments, each tray can be at a different temperature and pressure, where the distillation apparatus 104 bottom has the highest pressure and temperature. In some embodiments, while proceeding upwards along the distillation apparatus 104, the temperature and pressure decrease for each succeeding separation stage. In some instances, the vapor-liquid equilibrium for each feed component of the feed stream 106 in the distillation apparatus 104 reacts in a unique way to the different pressure and temperature conditions at each of the separation stages. That means, in some embodiments, each component establishes a different concentration in the vapor and liquid phases at each of the separation stages, resulting in the separation of components in the feed stream 106. In some embodiments, to produce a desired amount of product of a certain purity, as discussed herein, the distillation apparatus 104 can be operated in such a way as to include trays in a range of about 10 to about 300, preferably in a range of about 20 to about 200, and most preferably, in a range of about 40 to about 140. In some embodiments, the trays can be positioned in the distillation apparatus 104 with a uniform distance between each tray.

As discussed herein, calculating the number of equilibrium stages needed to achieve a desired separation can be determined using the McCabe Thiele method, the Fenske equation, or simulation models. As one skilled in the art will appreciate, once the number of equilibrium stages in the distillation apparatus 104 is calculated using the methods mentioned, the range of actual trays (separation stages) can be determined using routine experimentation and/or trial and error.

In some embodiments, the top portion of the distillation apparatus 104 can be operated at a temperature of about thirty-five (35)° C. and a pressure in a range of about two (2) to about three (3) atmospheres gauge, while the base portion can be operated at a temperature in a range of about ninety-five (95) to about one hundred (100) ° C. Operating the top portion of the distillation apparatus 104 at about thirty-five (35)° C. can decrease the cost of operating the process since in some embodiments, cooling water can be readily available at that temperature from other parts of the plant process.

In some embodiments, the low temperature of the base portion can reduce the amount of ethylene oxide which is converted to glycol in the base of the column, increasing monoethylene glycol (MEG) selectivity. Monoethylene glycol can be produced from ethylene via the intermediate ethylene oxide, where ethylene oxide reacts with water to produce MEG in a glycol reactor, as discussed herein. Monoethylene glycol is an important raw material for industrial applications, including the use of MEG in the manufacture of polyester resins, films, and fibers. In addition, MEG is important in the production of antifreezes, coolants, aircraft anti-icers and deicers, and solvents.

In embodiments of the present disclosure, the feed stream 106 can be fed to the distillation apparatus 104 base below a first separation stage. In some embodiments, the first separation stage (e.g., the first tray) can be at a temperature in a range of about forty-eight (48)° C. to about fifty (50)° C. In addition, the temperature profile over the first several separation stages included in the distillation apparatus 104 can be steep in that the temperature decreases rapidly over the first several separation stages. In some embodiments, the distillation apparatus 104 base can be in a range of one-hundred (100)° C. to about one-hundred-ten (110)° C.; whereas the temperature of the first few separation stages can have a range of about forty-eight (48)° C. to about fifty (50) ° C. The steep temperature profile is due to the process where the feed stream 106, which is mostly water when it is fed to the distillation apparatus 104, transitions from this mostly water composition to a composition that is mostly ethylene oxide as the water is evaporated and condensed from the feed stream 106.

For the various embodiments, ethylene oxide of at least 99.7 weight percent purity 112 can be withdrawn from the distillation apparatus 104. In some embodiments, the ethylene oxide stream 112 is withdrawn via a side ethylene oxide exit stream at a side take-off 114 located between the top and bottom of the distillation apparatus 104. In some embodiments, the ethylene oxide of at least 99.7 percent purity stream 112 can be withdrawn in a gaseous state. The ethylene oxide of at least 99.7 percent purity 112 can also be withdrawn in a liquid state. For the various embodiments, it would also be possible to obtain purities less than 99.7%, if desired, with reduced separation stages and/or energy utilization (heating and cooling). As discussed herein, in some embodiments, the distillation apparatus 104 can have eighty-six (86) trays. In such embodiments, the side take-off 114 can be located at a tray in a range of tray seventy-five (75) to tray eighty-six (86), as numbered from the bottom of the distillation apparatus 104 towards the top. Withdrawing the ethylene oxide of at least 99.7 percent purity 112 from a side take-off that is located below the top of the column can aid in removing trace light impurities (e.g., carbon dioxide, formaldehyde), as well as inert gases from the ethylene oxide exit stream, as discussed herein.

For the various embodiments, it is recognized that the location of the side take-off 114 for the various embodiments of the present disclosure is scalable based on the total number of separation stages and/or the efficiency of the separation. For example, where the distillation apparatus has more separation stages than eighty-six trays, such as 100 trays, the side take-off 114 can be located in a range of tray eighty-seven (87) to one hundred (100).

An impurity fraction 116 can be withdrawn via a top impurity exit stream at a top take-off 118 located on the top of the distillation apparatus 104. The impurity fraction 116 can include impurities as well as inert gases. In some embodiments, the impurity fraction 116 exits the distillation apparatus 104 from a condenser 124 located internally at the top of the distillation apparatus 104. The condenser 124 can also be located outside the distillation apparatus 104. In some embodiments, the condenser 124 can condense ethylene oxide that is still in vapor form at the top of the distillation apparatus 104 and return the condensed ethylene oxide to the distillation apparatus 104 as reflux. Returning the condensed ethylene oxide to the distillation apparatus 104 as reflux can improve the separation between ethylene oxide and the gases in the impurity fraction 116 by allowing additional condensation and vaporization to occur within the distillation apparatus 104. Also, the impurity fraction 116 can, in some embodiments, be vented, or the impurity fraction 116 can be routed to other reactors or columns in the ethylene oxide processing plant.

For the various embodiments, is it also possible to introduce an addition compound into the distillation apparatus 104. FIG. 1 illustrates a first feed point 125 and a second feed point 126, where one or more addition compounds can be introduced into the distillation apparatus 104. As used herein, addition compounds includes those independently stable compounds that are capable of combining with an impurity compound (e.g., formaldehyde) by means of van de Waals' forces, coordinate bonds, or covalent bonds to form an adduct. An example of a suitable addition compound can include, but is not limited to, water, which can include degassed water, de-mineralized water, and/or boiler feed water. Other addition compounds may also be possible.

For the various embodiments, the resulting adduct is heavier than the impurity compound itself, which causes the impurity to fall to the bottom of the distillation apparatus, where it can be removed in the aldehyde enriched fraction, as discussed herein. This process allows for the removal of impurities that have a boiling point close to the desired product (e.g., ethylene oxide) without the need of adding additional separation stages (or reflux flow) to the distillation apparatus.

For the various embodiments, the first feed point 125 can be located above the side take-off 114, and the second feed point 126 can be located below the side take-off 114. Other locations for the first and second feed points are also possible, where a consideration for this location could include where the fractions of the desirable product and the impurities have similar boiling points under the given conditions. It is also possible that different addition compounds and/or different addition rates of the addition compounds can be used at the first and/or second feed points along the distillation apparatus 104, depending on the given circumstances and conditions. It is also possible that less than all of the available feed points can be used to introduce an addition compound into the distillation apparatus 104 (e.g., could use either or both the first and second feed points).

In some embodiments, the impurity fraction 116 can include at least one of carbon dioxide, oxygen, nitrogen, argon, traces of formaldehyde, and other light impurities made in the base of the distillation apparatus 104, for example, nitric oxide.

An aldehyde enriched fraction 122 can be removed as a bottom aldehyde exit stream from the distillation apparatus 104 and can be fed to a glycol reactor 123 without further processing. As used herein, "without further processing" refers to sending the aldehyde enriched fraction 122 directly to the glycol reactor 123 without further purification, distillation, and/or addition of water. In addition, in some embodiments, the aldehyde enriched fraction 122 can be preheated in a heat exchanger before entering the glycol reactor 123.

Rather than adding water to the aldehyde enriched fraction 122, the distillation apparatus 104 can be operated in such a way that the aldehyde enriched fraction 122 is produced with a desired ratio of ethylene oxide to water. For example, the desired ratio of ethylene oxide to water can be controlled by altering the amount of product withdrawn as pure ethylene oxide in the ethylene oxide stream 112. In some embodiments, the weight ratio of water to ethylene oxide can range from about 6:1 to about 30:1.

In some embodiments, the glycol hydration of ethylene oxide and water can be employed without catalyzation. In such embodiments, the reaction in the glycol reactor 123 can produce a mixture of monoethylene glycol (MEG), diethylene glycol (DEG), and triethylene glycol (TEG). The product mix can be controlled by adjusting the ratio of water to ethylene oxide. The reaction can also produce aldehydes, croton aldehydes, acetate, and other polymers. In some embodiments, the glycol reactor 123 can be operated at a temperature in a range of about one hundred thirty (130)° C. to about two hundred fifty (250)° C. and a pressure in a range of about three (3.0) to about four (4.0) megapascals (MPa).

In some embodiments, the aldehyde enriched fraction 122 can include aldehydes at a level 1.3 times higher than the aldehydes in the feed stream 106. In some embodiments, the aldehyde enriched fraction 122 can include about zero (0) percent to about twenty (20) percent by weight ethylene oxide, preferably zero (0) to about seven (7) percent by weight ethylene oxide, and most preferably about seven (7) percent by weight ethylene oxide. The aldehyde enriched fraction 122 can also include about eighty (80) percent to about one hundred (100) percent by weight water, preferably eighty-five (85) to about one hundred (100) percent by weight water, and most preferably ninety-three (93) percent by weight water, and aldehydes in a range of about 1.3 to thirteen (13) ppm by weight. As will be appreciated by one skilled in the art, the pre-startup condition in the distillation apparatus 104 can contain zero ethylene oxide (i.e., a water run), and the process can then make a smooth transition to normal operating concentrations through startup followed by ramping up to normal operating conditions, as have been described herein.

In some embodiments, the distillation apparatus can be operated to distill the feed stream to produce the impurity fraction 116 and the aldehyde enriched fraction 122 while stopping the production of the ethylene oxide of at least 99.7 percent purity stream 112.

For the various embodiments, the ethylene oxide distilled according to the present disclosure can be processed to provide further downstream products, such as, for example, 1,2-diols, 1,2-diol ethers, 1,2-carbonates, and alkanolamines. Since the present disclosure provides improvements in the separation and purity of the ethylene oxide, it is contemplated that the improvements provided herein will carry forward to provide improvements to these downstream processes and/or products. Improved methods for the production of 1,2-diols, 1,2-carbonates, 1,2-diol ethers and alkanolamines are thus also provided herein.

The conversion of ethylene oxides into 1,2-diols or 1,2-diol ethers may comprise, for example, reacting the ethylene oxide with water, suitably in the presence of an acidic or basic catalyst. For example, for preferential production of the 1,2-diol over the 1,2-diol ether, the ethylene oxide may be reacted with a tenfold molar excess of water, in a liquid phase reaction in the presence of an acid catalyst, e.g., 0.5-1.0 wt % sulfuric acid, based on the total reaction mixture, at 50-70° C. at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternatively, 1,2-diol ethers may be prepared by converting the ethylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of ethylene oxide distilled according to the present disclosure into alkanolamines may comprise, for example, reacting the ethylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

It is to be understood that the above description has been made in an illustrative fashion, and not a restrictive one. Although specific embodiments have been illustrated and described herein, those of ordinary skill in the art will appreciate that other component arrangements can be substituted for the specific embodiments shown. The claims are intended to cover such adaptations or variations of various embodiments of the disclosure, except to the extent limited by the prior art.

In the foregoing Detailed Description, various features are grouped together in exemplary embodiments for the purpose of streamlining the disclosure. This method of disclosure is not to be interpreted as reflecting an intention that any claim requires more features than are expressly recited in the claim. Rather, as the following claims reflect, inventive subject matter lies in less than all features of a single disclosed embodiment. Thus, the following claims are hereby incorporated into the Detailed Description, with each claim standing on its own as a separate embodiment of the invention.

What is claimed:

1. A process for distilling ethylene oxide from a feed stream, the process comprising:
    introducing the feed stream, wherein the feed stream includes ethylene oxide and an amount of aldehyde, into a heat exchanger to heat the feed stream;
    feeding the heated feed stream to a base of a distillation apparatus located below a first separation stage of a plurality of separation stages that are numbered from a bottom of the distillation apparatus to a top of the distillation apparatus;
    removing from the distillation apparatus an impurity fraction as a top exit stream located at a top take-off on the distillation apparatus;
    removing from the distillation apparatus an ethylene oxide stream of at least 99.7 weight percent purity, based on the total weight of the ethylene oxide stream; and
    removing from the distillation apparatus an aldehyde enriched fraction as a bottom stream.

2. The process of claim 1, where the process includes heating a liquid content of the distillation apparatus in situ below a first separation stage of the distillation apparatus.

3. The process of claim 1, where the process includes feeding the aldehyde enriched fraction without further purification to a glycol reactor.

4. The process of claim 1, including introducing an addition compound into the distillation apparatus to combine with an impurity compound in the distillation apparatus.

5. A process for converting ethylene oxide distilled according to the process of claim 1 through reaction with water into a 1,2-diol or a 1,2-diol ether.

6. A system to distill ethylene oxide, comprising:
a heat exchanger; and
a distillation apparatus operably connected to the heat exchanger, where the heat exchanger heats a feed stream that enters a base of the distillation apparatus below a first separation stage of a plurality of separation stages that are numbered from a bottom of the distillation apparatus to a top of the distillation apparatus, and where the distillation apparatus includes:
a top exit stream;
a side take-off located between a top and a bottom of the distillation apparatus, where an ethylene oxide stream is removed as a side stream at the side take-off; and
a bottom exit stream, where the bottom exit stream is in direct connection with a glycol reactor.

7. The system of claim 6, where the plurality of separation stages include eighty-six (86) separation stages and the side take-off is located at a separation stage in a range of separation stage seventy-five (75) through eighty-six (86).

8. The system of claim 6, where a top portion of the distillation apparatus is at a temperature of about thirty-five (35) degrees Celsius.

9. The system of claim 8, where a base portion of the distillation apparatus is at a temperature in a range of about ninety-five (95) to about one hundred (100) degrees Celsius.

10. The system of claim 9, where the first separation stage of the distillation apparatus is at a temperature in a range of about forty-eight (48) to about fifty (50) degrees Celsius.

11. The system of claim 6, where the feed stream includes, based on its weight, ethylene oxide in a range of about five (5) percent to about twenty (20) percent by weight.

12. The system of claim 6, where the feed stream includes aldehydes in a range of about one (1) to about one hundred (100) parts per million by weight.

13. The system of claim 12, where the bottom exit stream includes an aldehyde enriched fraction having ethylene oxide in a range of about seven (7) percent to about twenty (20) percent by weight and water in a range of about eighty (80) percent to about ninety-three (93) percent by weight, based on total weight of the aldehyde enriched fraction.

14. The system of claim 6, where the distillation apparatus has structured packing having a required height equivalent of about fifty separation stages and one to five trays in a bottom portion of the distillation apparatus.

15. The system of claim 6, where the distillation apparatus includes an addition compound inlet into the distillation apparatus in an upper portion of the distillation apparatus.

16. A process, comprising:
introducing a feed stream including ethylene oxide and an amount of aldehyde into a heat exchanger to heat the feed stream;
feeding the heated feed stream to a base of a distillation apparatus located below a first separation stage of a plurality of separation stages that are numbered from a bottom of the distillation apparatus to a top of the distillation apparatus;
distilling the feed stream in the distillation apparatus to produce an impurity fraction and an aldehyde enriched fraction, where the aldehyde enriched fraction includes 1.3 times more aldehyde than the amount in the feed stream, ethylene oxide in a range of about seven (7) percent to about twenty (20) percent by weight and water in a range of about eighty (80) percent to about ninety-three (93) percent by weight, based on total weight of the aldehyde enriched fraction; and
feeding the aldehyde enriched fraction without further processing to a glycol reactor.

17. The process of claim 16, where distilling the feed stream produces an ethylene oxide stream of at least 99.7 weight percent purity.

18. The process of claim 16, where the aldehyde enriched fraction includes aldehydes in a range of about 1.3 to 13 ppm by weight.

19. The process of claim 16, where the process includes reacting the ethylene oxide and water in the aldehyde enriched fraction to produce monoethylene glycol, diethylene glycol, and triethylene glycol.

* * * * *